United States Patent
Li (10) Patent No.: US 7,487,773 B2
(45) Date of Patent: Feb. 10, 2009

(54) GAS FLOW CONTROL METHOD IN A BLOWER BASED VENTILATION SYSTEM

(75) Inventor: Kun Li, Milpitas, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 727 days.

(21) Appl. No.: 10/949,853

(22) Filed: Sep. 24, 2004

(65) Prior Publication Data

US 2006/0065270 A1 Mar. 30, 2006

(51) Int. Cl.
*A61M 16/00* (2006.01)
(52) U.S. Cl. .............................. 128/204.18; 128/204.23
(58) Field of Classification Search ............ 128/204.21, 128/204.23, 204.18, 200.24, 207.22, 204.22
See application file for complete search history.

(56) References Cited

U.S. PATENT DOCUMENTS

| | | | |
|---|---|---|---|
| 3,741,208 A | 6/1973 | Jonsson et al. | |
| 3,923,056 A | 12/1975 | Bingmann et al. | |
| 3,961,627 A | 6/1976 | Ernst et al. | |
| 3,972,327 A | 8/1976 | Ernst et al. | |
| 4,281,651 A | 8/1981 | Cox | |
| 4,345,612 A | 8/1982 | Koni et al. | |
| 4,421,113 A | 12/1983 | Gedeon et al. | |
| 4,971,049 A | 11/1990 | Rotariu et al. | |
| 5,259,373 A | 11/1993 | Gruenke et al. | 128/204.23 |
| 5,271,389 A | 12/1993 | Isaza et al. | |
| 5,645,054 A | 7/1997 | Cotner et al. | 128/204.23 |
| 5,694,923 A * | 12/1997 | Hete et al. | 128/204.18 |
| 6,213,119 B1 | 4/2001 | Brydon et al. | 128/204.23 |
| 6,299,581 B1 * | 10/2001 | Rapoport et al. | 600/484 |
| 6,488,634 B1 | 12/2002 | Rapoport et al. | 600/538 |
| 6,571,795 B2 * | 6/2003 | Bourdon | 128/204.23 |
| 6,622,726 B1 * | 9/2003 | Du | 128/204.26 |
| 2001/0004894 A1 | 6/2001 | Bourdon | 128/204.23 |
| 2003/0062044 A1 | 4/2003 | Berthon Jones et al. | 128/204.18 |

FOREIGN PATENT DOCUMENTS

| | | |
|---|---|---|
| DE | 102 53 935 B3 | 3/2004 |
| EP | 0 371 597 A2 | 6/1990 |
| GB | 2 101 895 A | 1/1983 |
| WO | WO 89/10768 | 11/1989 |
| WO | 00/67826 | 11/2000 |
| WO | 01/32069 A2 | 5/2001 |

OTHER PUBLICATIONS

PCT International Search Report & Written Opinion for Application PCT/US2005/033816, 16 pages, Mailed Dec. 22, 2005.

* cited by examiner

*Primary Examiner*—Steven O Douglas
(74) *Attorney, Agent, or Firm*—Baker Botts L.L.P.

(57) ABSTRACT

The invention is directed to a system and method for controlling the flow of gas from a medical ventilator into a patient's lungs. The control system provides for a non-linear feedforward controller to correct for disturbances caused by back pressure at the outlet of the blower of the medical ventilator. For this purpose, a pressure transducer is provided to measure the back pressure. Additionally, the invention allows for a feedback controller to correct for the differences between the rate of the actual gas flow and the targeted gas flow rate. For this purpose a flow rate transducer is provided. The control system may account for each of the gas flow rate error and the back pressure disturbance to provide for a quick and accurate adjustment to achieve the targeted gas flow rate.

27 Claims, 7 Drawing Sheets

GAS FLOW CONTROL METHOD IN A BLOWER BASED VENTILATION SYSTEM

FIELD OF THE INVENTION

This invention relates generally to the field of medical ventilators used to assist breathing in critical and non-critical patients. More particularly, this invention relates to a method and system for controlling the gas flow rate from a medical ventilator having a variable speed blower.

BACKGROUND OF THE INVENTION

Modern medical ventilators are designed to ventilate a patient's lungs with respiratory gas, and to thereby assist a patient when the patient's ability to breathe on his own is somehow impaired. As research has continued in the field of respiration therapy, a wide range of ventilation strategies have been developed. For example, pressure assisted ventilation is a strategy often available in patient ventilators and includes the supply of pressure assistance when the patient has already begun an inspiratory effort. With such a strategy, it is desirable to immediately increase the pressure after a breath is initiated in order to reach a target airway pressure for the pressure assistance. This rise in pressure in the patient airway which supplies respiratory gas to the patient's lungs allows the lungs to be filled with less work of breathing by the patient. Conventional pressure assisted ventilator systems typically implement a gas flow control strategy of stabilizing pressure support after a target pressure is reached to limit patient airway pressure. Such a strategy also can include programmed reductions in the patient airway pressure after set periods of the respiratory cycle in order to prepare for initiation of the next patient breath.

Conventional ventilators typically provide breath inhalation support at regular intervals, or at intervals triggered by a patient's spontaneous inspiration effort. The method of controlling the gas flow requires actuation of a gas flow valve. Errors in the delivery of gas flow as compared to the desired gas flow at the appropriate time can occur due to lag time between the onset of patient inspiratory effort and actual valve response time, regulator response, and valve gain variations. Although typical flow controllers may utilize a feedforward flow control gain component and various types of feedback error correction, such as proportional, integral, and derivative error feedback control, to compensate for real time disturbances that occur in the system, such systems frequently have difficulty in correcting for any sustained errors that occur periodically in the system.

Another method of controlling the gas flow rate has been the use of variable speed blowers or fans. The speed of such blowers can be rapidly increased or decreased to impart a desired rate of flow. This allows greater flexibility in controlling each inspiration and exhalation. The rapid rate of change in the gas flow allows the ventilator to vary the rate of flow multiple times or even continuously within the time span of a single breath. Such a ventilator can gently respond to the patient's initiation of inspiration and exhalation only when such responses are carefully monitored. Furthermore, a ventilator needs to make rapid and repeated adjustment to respond accordingly. A blower based ventilator is capable of such gas flow control.

Conventional flow control in a blower based ventilation system uses an electronic feedback controller to control the gas flow rate. As an example, a target flow rate can be input into a ventilator's electronic interface to initiate the control function. An electronic motor controller may be configured to control the speed of a motor attached to the blower or fan. Under ideal conditions, the speed of the motor determines the gas flow rate at the blower outlet. However, the static pressure at the blower outlet will affect the actual flow rate. Variations in the static pressure may generate variations in the actual flow rate even though the speed of the motor remains constant.

To account for variations in the static pressure, conventional blower based ventilators have relied upon an electronic feedback controller connected to an airflow transducer to measure the actual airflow generated by the blower. Such feed-back controllers have relied upon the proportional-integral-derivative method of control. This method is effective only under conditions where the static pressure does not change significantly. Unfortunately, in the environments experienced by medical ventilators, the static pressure may change significantly. Moreover, while blowing gas into a patient's lungs, the static pressure (experienced in this case as the back pressure created by the lungs) varies over time. This may ultimately cause large deviations from the target flow rate.

Therefore, despite the ability to rapidly vary the actual flow rates, conventional blower-based ventilator systems have been unable to accurately maintain a target flow rate. This is due, in part, to a control system that must continually adjust to an actual flow rate which varies over time. Such control systems continually change the motor speed to alter the actual flow rate which is also continuously changing in response to changes in the back pressure of the lungs. At worst, this method will produce an unstable control system which progressively deviates from the target flow rate. At best, this method will produce a minimally stable control system which continuously oscillates about the target flow rate.

What has been needed and heretofore unavailable in a blower based medical ventilator in a control system that accurately compensates for environmental pressures to stably maintain a target flow rate. The present invention fulfills this and other needs.

SUMMARY OF THE INVENTION

The present invention provides a system and method for providing a correction to a signal controlling a variable speed motor and blower within a medical ventilator system. The desired control system provides a feedforward controller which responds to the existing back pressure at the outlet of the blower. The feedforward controller accurately predicts the effect of the back pressure on the changes required in gas flow and required motor speed. In a preferred embodiment, the control system also includes a feedback controller which responds to the actual gas flow induced by the blower. In such an embodiment, the feedfoward controller and the feedback controller work in unison to establish a target gas flow.

Briefly and in general terms, the control system of the present invention is configured to control the airflow generated by a blower based medical ventilator. The medical ventilator connects to a patients lungs for supporting breathing. Typically, the ventilator includes at least one gas flow hose which can be connected either over a patient's nose and mouth or directly into the patient's trachea through the neck. Blower based ventilator systems include a variable speed blower (or "fan") connected to the opposite end of the hose. The blower is configured to induce a gas flow through the hose and inflate the lungs. Ventilators employ a "respiratory gas" which can be either a standard air mix or an oxygen rich equivalent.

The blower of the desired medical ventilator system is run by an electric motor which in turn is controlled by an electronic motor controller. The electronic motor controller provides a pulse width modulated (PWM) signal to the electric motor. By varying the pulse width of this signal, the electronic motor controller can vary the speed at which the motor runs. The electronic motor receives feedback from the motor which indicates actual motor speed. The electronic motor can thereby correct its PWM signal to correct the actual motor speed to the target motor speed. Of course, the target and actual motor speeds, correspond to the target and actual fan speeds respectively. Typically, the corresponding ratio between motor speed and fan speed is one to one. However, other corresponding ratios can be achieved.

To initiated the ventilation process a physician/operator may input a target flow rate into the ventilator control system. Similarly, the physician operator may also input another parameter (such as volume and or air pressure) that could be used to determine a target flow rate. The electronic motor controller is programmed to calculate at least a target fan speed which corresponds to the target flow rate. The electronic controller then sends the appropriate PWM signal to the motor to achieve said target fan speed.

The present medical ventilator includes at least an electronic feedforward controller which modifies the target fan speed based on the back pressure currently experienced by the blower. Even prior to ventilation, a patient's lung will present at least an initial pressure (possibly greater than, or even less than ambient pressure). This pressure will be experienced as back pressure at the blower outlet.

Increased back pressure at the blower outlet will decrease the gas flow rate at any given fan speed. Thus, the actual flow rate will deviate from the target flow rate based on differing back pressure. Moreover, during inspiration, when gas flows into a patient's lung, the back pressure will increase over time. That is, as the lungs fill with respiratory gas the pressure within the lungs (and at the blower outlet) increases. This increase in pressure is not a linear function over time for a given rate of gas flow.

To correct the target fan speed to accurately induce the target fluid flow, the electronic feedforward controller is programmed to correct not only for the currently measured back pressure, but also for the change experienced over time in the back pressure due to the gas flow. This is a non-linear correction based upon the non-linear correspondence between time and pressure for any given fan speed.

To measure back pressure, a pressure transducer is included with the medical ventilator. This transducer may be placed anywhere downstream of the blower outlet, but is preferably located near the blower outlet. The pressure transducer is configured to transmit signals to the electronic feedforward controller. The transducer may be configured to continuously monitor the pressure or to take multiple measurements within a short time span.

The present medical ventilator may also include an electronic feedback controller which modifies the target fan speed based on the actual gas flow rate induced by the blower. This controller adjusts the target fan speed up or down in instances where the actual gas flow rate is less than or greater than the target flow rate respectively. This controller may operate on a proportional-integral-derivative ("PID") control system. Such a system operates on the basis of the measured error and rate of change of error between a set point and a process variable. In this instance, the set point is the target gas flow rate and the process variable is the actual gas flow rate. By tracking changes in the actual flow over time a PID control system makes iterative calculations of the proportional, integral and derivative parts of the calculation to determine the appropriate corrective action. A PID control system requires a gain value to be set for each of the proportional, integral and derivative parts of the calculation. Moreover, several different PID control equations of various complexities exist. The appropriate equations and gains are those that result in a rapid correction between the set point and process variable without undue oscillation of the control system. Determining these variables is a familiar process to those of skill in the art of control systems.

Measuring the actual gas flow rate the medical ventilator system requires a gas flow transducer. This transducer may be located anywhere downstream of the blower, but is preferably located near the blower outlet. The gas flow transducer is configured to transmit signals to the electronic feedback controller. The transducer may be configured to continuously monitor the gas flow rate or to take multiple measurements within a short time span.

Where both a feedforward controller and a feedback controller are in use, these controllers will ideally work together to make the most efficient control system. Thus, at any given time, the electronic motor controller will receive the required input to establish a single target fan speed which is optimally set to provide the target gas flow rate given the current actual gas flow rate and the current back pressure. This might be a calculation performed by the electronic motor controller. Alternatively, a separate device or circuit may be provided which is specifically designed to receive input from both the electronic feedforward controller and the electronic feedback controller and output an optimal target fan speed.

These and other features and advantages of the invention will become apparent from the following detailed description, taken in conjunction with the accompanying drawings, which illustrate, by way of example, the features of the invention.

DETAILED DESCRIPTION OF THE INVENTION

The present invention is directed to a control system for a medical ventilator. The control system described herein is applied to a blower-based medical ventilator system. A blower-based system uses a blower, often configured as a fan, to generate a flow of respirator gas into the lungs of a patient. The flow of gas is generated by the blower and delivered to the patient through a tube. The gas flow rate in a blower based medical ventilators may be controlled by the fan-speed of the blower. Thus a variable speed fan is a desirable feature of such systems. Variable speed fans may be operated by an electric motor and an electronic motor controller which varies the electrical input signal to the electric motor to vary the speed of the motor and fan.

Modern medical ventilators are carefully controlled to meet the varying needs of the patient. One goal of modem ventilators is to respond to and encourage independent breathing efforts by the patient. Meeting this goal requires continuous monitoring and controlling of the gas flowing into the patient's lungs often requiring multiple adjustments per second. A blower-based medical ventilator system may accomplish this by monitoring and adjusting the rate of gas flow exiting the blower to a target flow rate. This is complicated by the many variables which impact the actual flow rate generated by the blower.

Thus, the present invention is directed to a novel system and method for monitoring and adjusting the actual gas flow rate to accomplish a target flow rate. Preferably, this task is accomplished, at least in part, by utilizing a feedback control circuit which measures and tracks the difference between the actual flow rate and the target flow rate. Additionally, the system utilizes a feedforward control circuit which measures the back pressure experienced by the blower. These controllers each calculate an adjustment to the fan speed which will alter the actual gas flow rate to correct for the difference between the actual and target flow rates. These calculations and adjustments may be repeated many times per second. The result is a control system which accounts for environmental parameters to quickly and accurately adjust the actual gas flow rate to a target gas flow rate.

Figure 1:
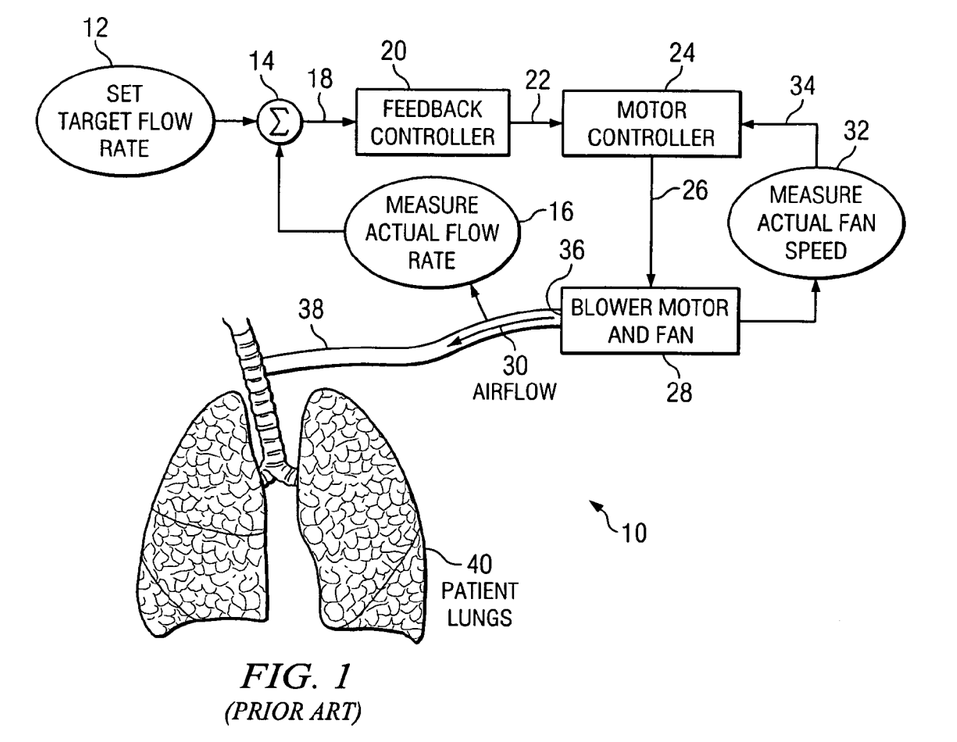
FIG. 1 is a block diagram of a conventional prior art flow control system in a medical ventilator.

Referring to FIG. 1, in a conventional prior art flow control system 10 in a patient ventilator a desired flow rate signal 12 is input to the flow control system at the summing junction 14 for a desired flow for a particular portion of a patient's breath cycle. The summing junction compares the desired flow rate signal with measured flow, and for this purpose also receives a feedback input of the measured flow 16 delivered flow to the patient, from one or more flow sensors or flow meters (not shown), which is subtracted from the desired flow rate signal in the summing junction, to provide an adjusted differential flow rate signal 18 to achieve the desired flow rate. The adjusted differential flow rate signal is received by a feedback controller 20, which provides a desired blower motor speed signal 22 based upon the adjusted differential flow rate signal. Typically, such flow control utilizes a feedback control mechanism such as a PID regulator, which combines a proportional gain circuit, an integral gain circuit, and a differential gain circuit that together form a PID control loop, the outputs of which are summed to provide an adjusted feedback signal. The blower motor speed signal is received by a motor controller 24, which provides a pulse width modulation (PWM) signal 26 to the blower or motor unit 28 for driving the ventilator blower at the appropriate speed to achieve the desired ventilation flow 30. A motor speed sensor 32 generates a motor speed feedback signal 34 which is received by the motor controller and compared with the blower motor speed signal, for gross adjustments of the motor speed. The ventilation flow is delivered to the patient from the blower outlet 36 through a ventilator hose 38.

The conventional prior art flow control system does not adjust the ventilator system for differences in the static or back pressure experience at the blower outlet 36. At all times during the operation of the ventilator system the blower outlet will experience a certain amount of pressure. This back pressure disturbance will increase due to the continuous flow of breathing gas provided by the ventilator to the patient. With a significantly changing flow, the back pressure generated by the patient's lungs 40 will have the same effect as a disturbance to the output flow of the blower. That is, the increase in pressure experienced as the lungs inflate will be exhibited as back pressure at the blower outlet which will impact the actual rate of flow. In general, with all other parameters (such as fan speed) remaining the same, an increase in back pressure will result in a decrease in the actual flow rate. However, the relationship between back pressure and actual flow rate is not a linear function.

With the conventional prior art feedback control system illustrated in FIG. 1, corrective action due to backpressure can only be taken after the flow rate has been affected by the back pressure. The conventional control system measures the actual flow rate exiting the blower outlet. As discussed above this flow rate is impacted not only by the static pressure at the blower outlet but by the backpressure induced by the flow of gas itself. However, the typical feedback control system corrects only for the present and past conditions experienced by the ventilator. Thus, once the feedback controller adjusts the fan speed to correct for the present and past actual flow rates, it then has to wait to measure the new actual flow rate to determine the impact the adjustment has had. Such a system may lead to large deviations from or oscillations about the target flow rate.

Figures 2, 3:
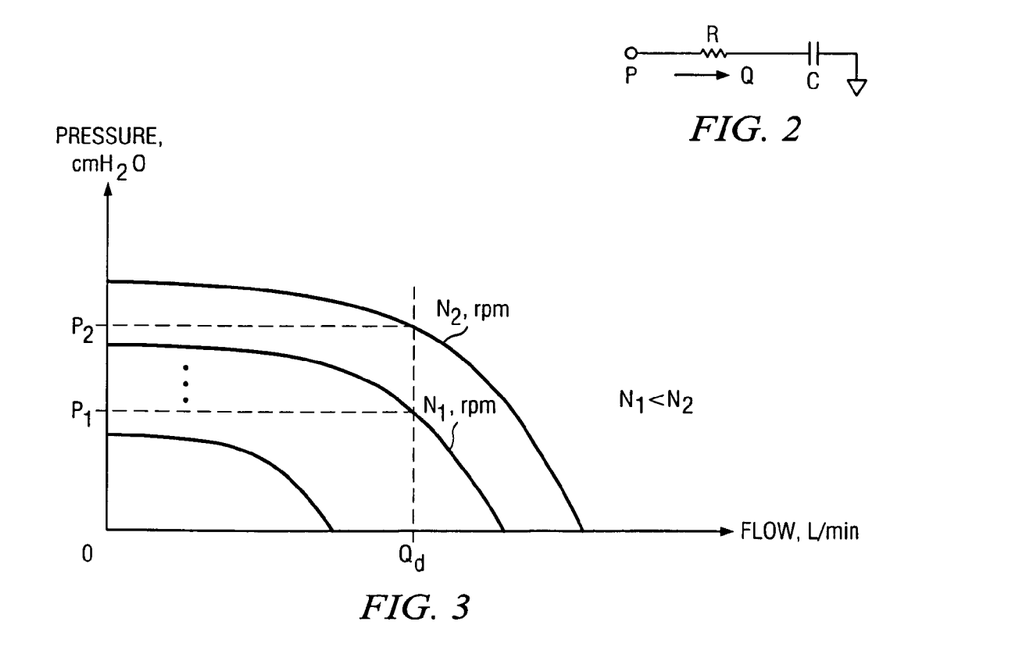
FIG. 2 is a block diagram of a simplified patient lung model.
FIG. 3 is a graph depicting performance curves for a blower based medical ventilator.

The nature of the disturbance to the airflow 30 due to the back pressure at the blower outlet can be better understood from consideration of a simplified patient lung model in FIG. 2, and the generalized blower performance curves shown in the FIG. 3.

In FIG. 2, the relationship between the gas flow 30 and the patient's lungs 40 is represented as an electrical circuit. P represents the positive pressure generated by the blower at the outlet of the blower and is analogous to a dc voltage applied to the circuit. Q represents the flow at the outlet of the blower, with appropriate units and is analogous to current in the circuit. R represents the patient airway resistance, with appropriate units and is analogous to a resistor in the circuit. C represents the compliance, with appropriate units and is analogous to a capacitor in the circuit.

As the gas flows into the lungs, the lungs begin to fill in a similar manner as current charging a capacitor. As the lungs become filled, they generate greater resistance to flow.

The pressure can be calculated by the following equation:

$$P = R \cdot Q + \int Q \, dt / C + P_0 \quad (1)$$

where, $P_0$ is the initial pressure inside the patient lung. The initial pressure can also be expressed as the static pressure or the ambient pressure at the blower outlet in the absence of airflow.

It is apparent from equation (1) that the pressure P at the outlet of the blower will change as breathing gas flows into the patient lung continuously. Therefore the relationship between Pressure and the gas flow rate is non-linear.

Referring to FIG. 3, depending upon the particular characteristics of the blower, there are different specific performance curves for the blower corresponding to different specific motor speeds. For instance, the middle curve 42 in FIG. 3 is a performance curve corresponding to a blower motor speed $N_1$. If the blower motor speed is kept constant, the flow rate will drop as the back pressure P at the blower outlet increases. In other words, if a target flow rate of $Q_d$ is required at a given back pressure $P_1$, the motor has to run at speed $N_1$. As the back pressure increases from $P_1$ to $P_2$, the speed of the motor must increase from $N_1$ to $N_2$ in order to keep a constant flow rate, $Q_d$. Although fan speed is preferably equal to the motor speed, using gears may change the ratio between the fan and motor.

A conventional feedback controller will wait until the flow rate changes before feedback action can be taken, and back pressure disturbances in the output flow are inevitable. A non-linear feedforward controller 64 in FIG. 5 allows the blower in a medical ventilator to perform effectively regardless of changing back pressure. Preferably the non-linear feedforward controller can make adjustments in the motor control signal in response to the changes in the back pressure. With a non-linear feedforward controller, it is possible to compensate for the nonlinear effect of the measured disturbance pressure on the actual flow rate before the flow rate is affected. Therefore, the perfect disturbance rejection (in other words, the perfect performance correction) to correct for backpressure is possible with a non-linear feedforward controller. This is not possible with a feedback controller.

Figure 5:
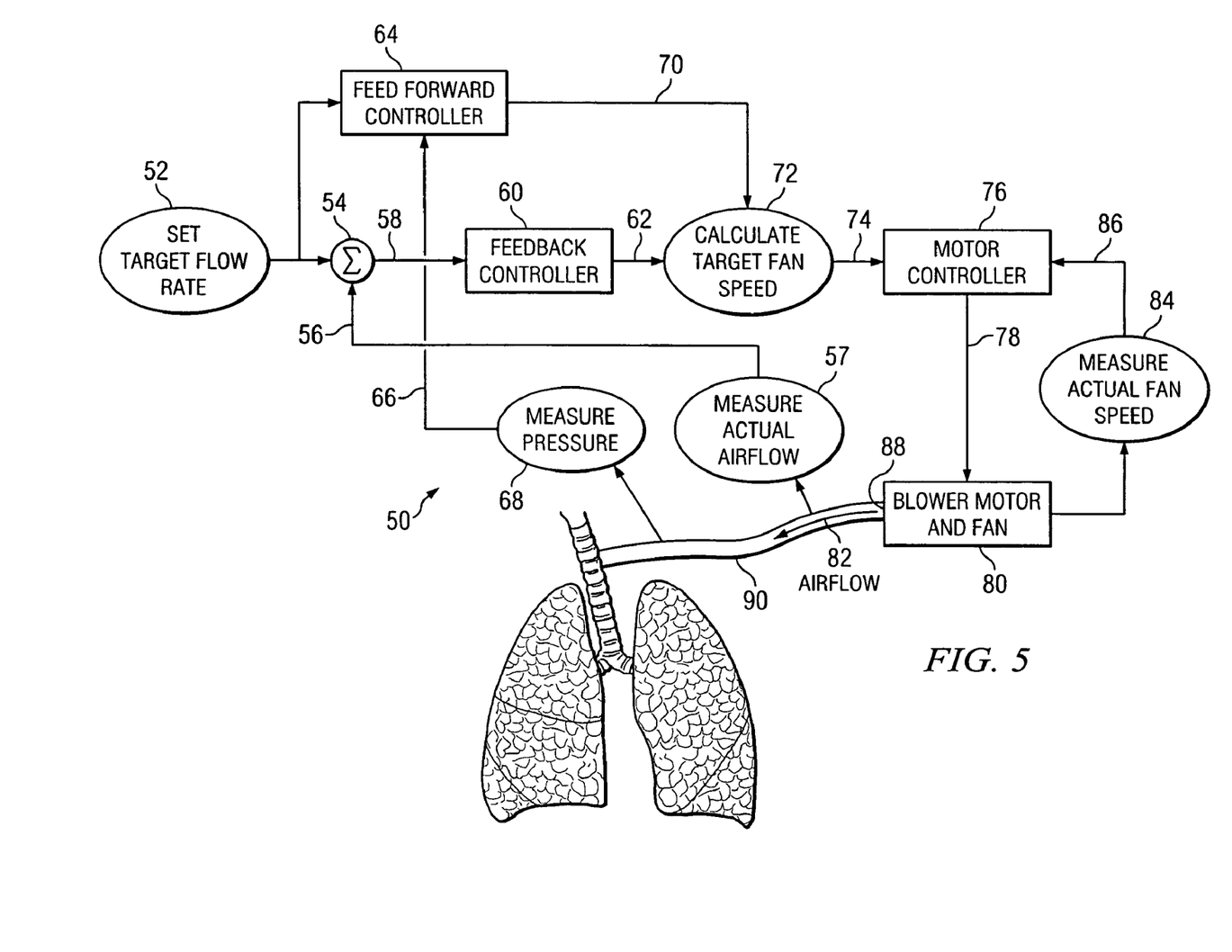
FIG. 5 is a block diagram of a control system in a medical ventilator incorporating the present invention.

The function of the feedforward controller is to calculate a desired motor speed $N_2$ when the pressure has changed to $P_2$. Preferably, the new back pressure at the blower outlet 36 is measured by a pressure transducer located near the blower outlet. The desired motor speed $N_2$ can be determined when the pressure changes to $P_2$, according to the fan law, described in the following equation:

$$P = \alpha \cdot N^2 + \beta \cdot N \cdot Q + \gamma \cdot Q^2 \quad (2)$$

The variables $\alpha$, $\beta$ and $\gamma$ may be obtained by fitting the experimental data via least square method described in the following. These variables reflect the specific fan and motor performance.

Suppose a set of measurements including flow, pressure, and speed has been taken for a particular blower. The number of measurements is n. Therefore we assume the following:

$$\alpha \cdot N_k^2 + \beta \cdot N_k \cdot Q_k + \gamma \cdot Q_k^2 = P_k + e_k \text{ for } k = 1, 2, 3, \ldots, n \quad (3)$$

Figure 4:
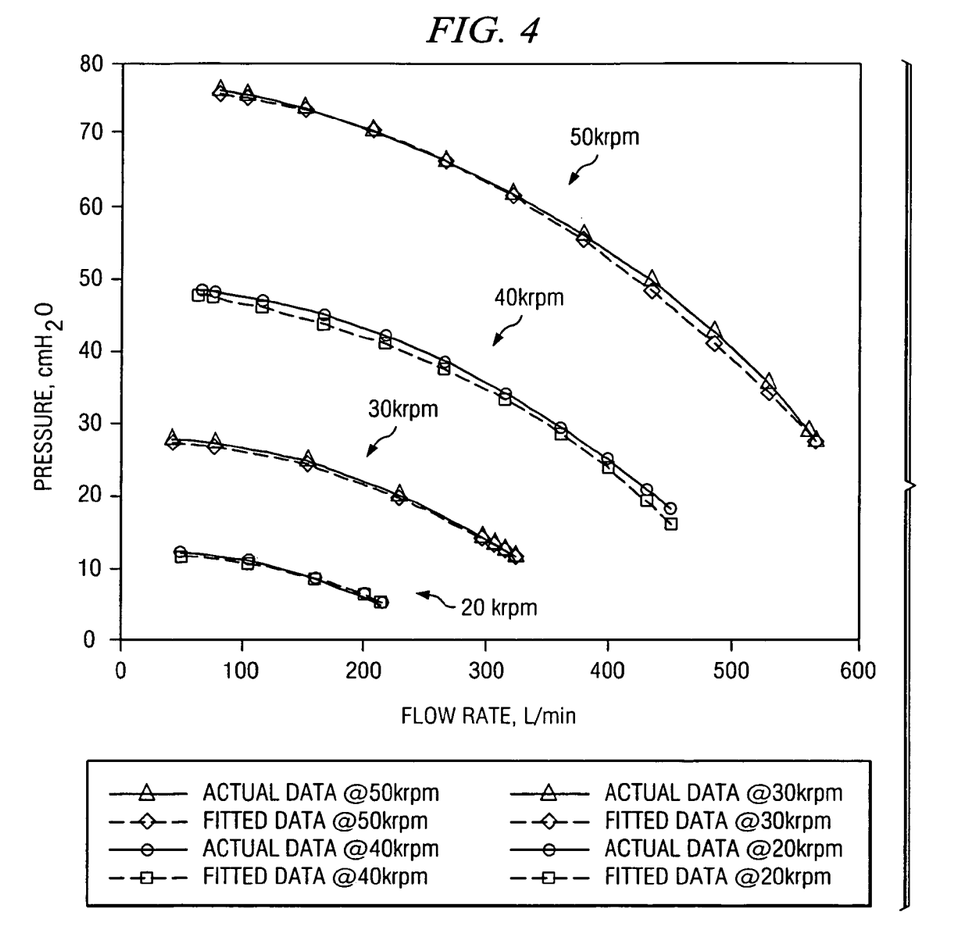
FIG. 4 is a graph depicting performance curves for a blower based medical ventilator with specific data points.

The variable e reflects the measurement error. Then, a standard least square problem can be formulated to solve for $\alpha$, $\beta$, and $\gamma$. For the data shown in FIG. 4, $\alpha = 0.03028$, $\beta = 0.00018$, $\gamma = -0.00016$ are the solutions for the least square fittings.

Given the pressure measurement P and the desired flow rate Q, the desired motor speed can be solved via the following quadratic equation:

$$N = \{-\beta \cdot Q + [(\beta \cdot Q)^2 - 4\alpha \cdot (\gamma \cdot Q^2 - P)]^{1/2}\}/2\alpha \quad (4)$$

For a general variable speed motor controller, the relationship between the speed control signal u, and the speed N is linear as expressed in the following:

$$N = k \cdot u \quad (5)$$

where, k is a constant provided by the motor controller manufacturer or measured by the user via experiment.

In case equation (1) does not hold due to the other factors, it can be rewritten in a more general form as the following:

$$N = f(u) \quad (6)$$

where, $f(\cdot)$ is a function or just as simple as a look-up table created through the experiment.

So in order to reach the required speed, the desired control input can be obtained as follows:

$$u = f^{-1}(N) \quad (7)$$

where, $f^{-1}()$ represents the inverse function of $f()$.

A feedforward controller can make adjustments in the motor control signal in response to the observed changes in the back pressure. With a feedforward controller, compensation for the effect of the measured disturbance pressure is possible before the flow rate is affected. The immediate implication is therefore that rejection of significant back pressure disturbances, an absolute impossibility with only feedback control, is possible with a feedforward controller.

Referring to FIG. 5, a preferred embodiment of the invention provides for a flow control system 50 with feedforward control in a patient ventilator (not shown). A target flow rate signal 52 is input to the flow control system at the summing junction 54 for a desired flow for a particular portion of a patient's breath cycle. The summing junction compares the desired flow rate signal with measured flow, and receives a feedback input of the measured flow 56 delivered to the patient, from one or more flow sensors or flow meters 57, which is subtracted from the desired flow rate signal in the summing junction, to provide an adjusted differential flow rate signal 58 to achieve the desired flow rate. The adjusted differential flow rate signal is received by a PID feedback controller 60, having an output signal 62. A non-linear feedforward controller 64 receives the desired flow rate signal as well as a measured pressure signal 66 from a back pressure sensor 68, and the non-linear feedforward controller provides an output feedforward signal 70 based upon the desired flow rate signal and the measured pressure signal. The summing and calculating junction 72 receives and sums the PID feedback controller output signal and the output feedforward signal. The summing and calculating junction calculates a target motor speed based on the target flow projected by both the feedback controller and the feed forward controller. The result is an adjusted blower motor speed signal 74. The blower motor speed signal is received by a motor controller 76, which provides a pulse width modulation (PWM) signal 78 to the blower or motor unit 80 for driving the ventilator blower at the appropriate speed to achieve the desired ventilation flow 82. A motor speed sensor 84 generates a motor speed feedback signal 86 which is received by the motor controller and compared with the blower motor speed signal, for gross adjustments of the motor speed. The ventilation flow is delivered to the patient at the blower outlet 88, which results in a back pressure 90.

Figure 6:
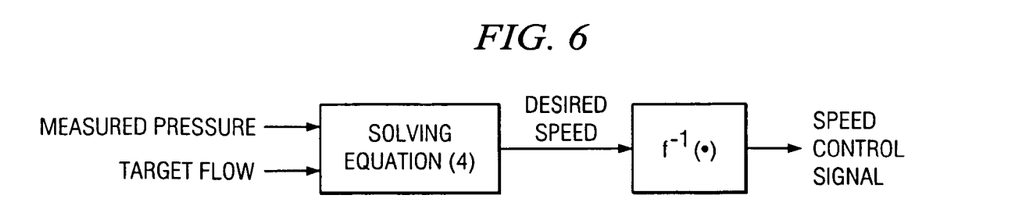
FIG. 6 is a block diagram depicting the implementation of a non-linear feed forward controller.

Referring to FIG. 6 the feedforward controller 64 operates in the described manner. The value of the measured pressure is inserted into the variable P in equation (4). The value of the target flow is inserted into the variable Q in equation (4). The values for $\alpha$, $\beta$ and $\gamma$ in equation (4) are preprogrammed from experimentation with the fan configuration as described by FIG. 3 and solving equation (3). The feedforward controller solves equation (4) to determine the target motor speed.

The preferred method of the invention has been tested in a pneumatic platform with control algorithm being implemented in Simulink in real-time. Experimental data (FIGS. 7 and 8) shows the proposed method achieved much better flow control performance compared to the results from conventional feedback controller.

Figure 7A:
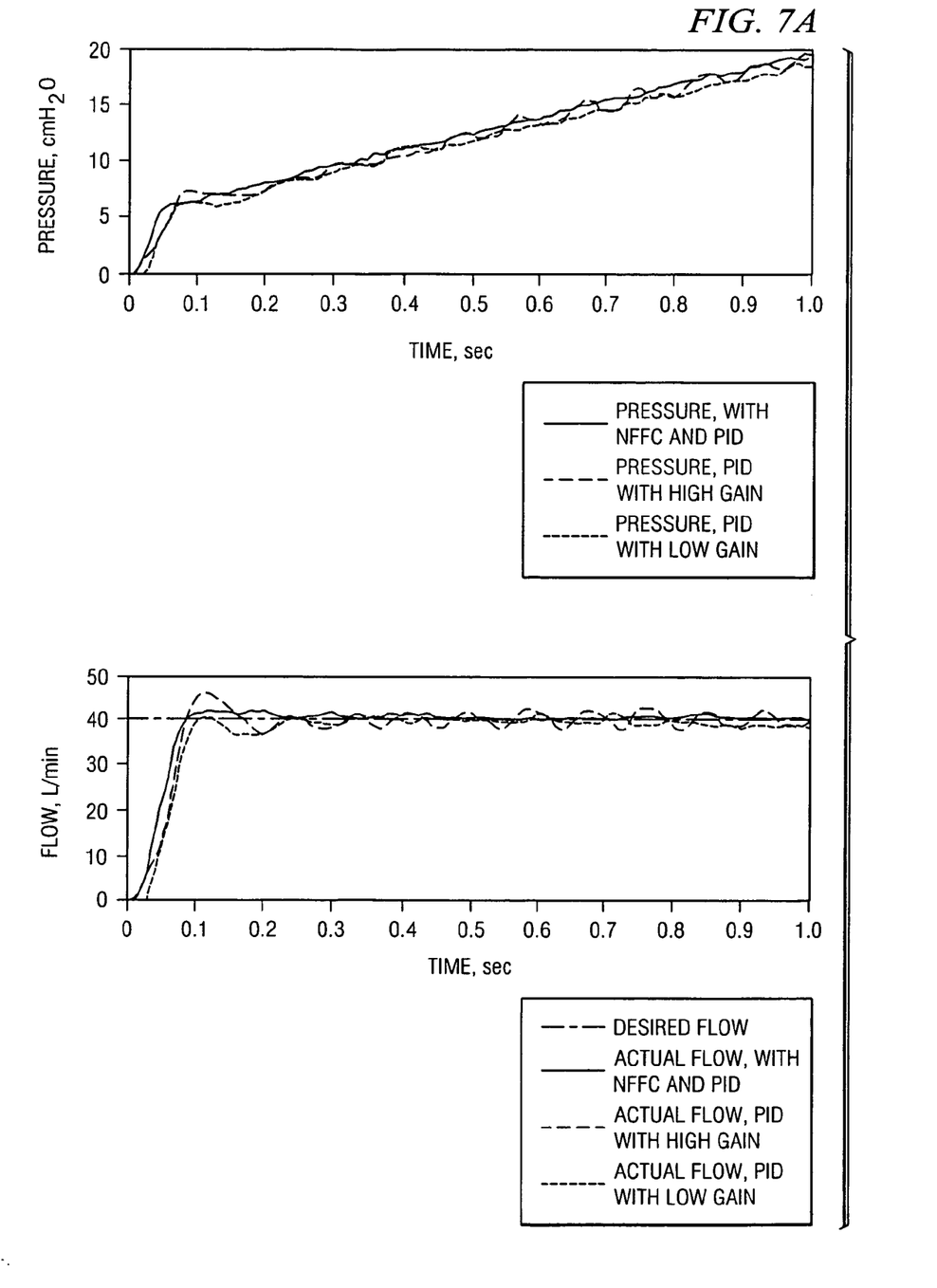
FIGS. 7A and 7B are graphs depicting the performance of control systems in an example requiring constant gas flow rate.
Figure 7B:
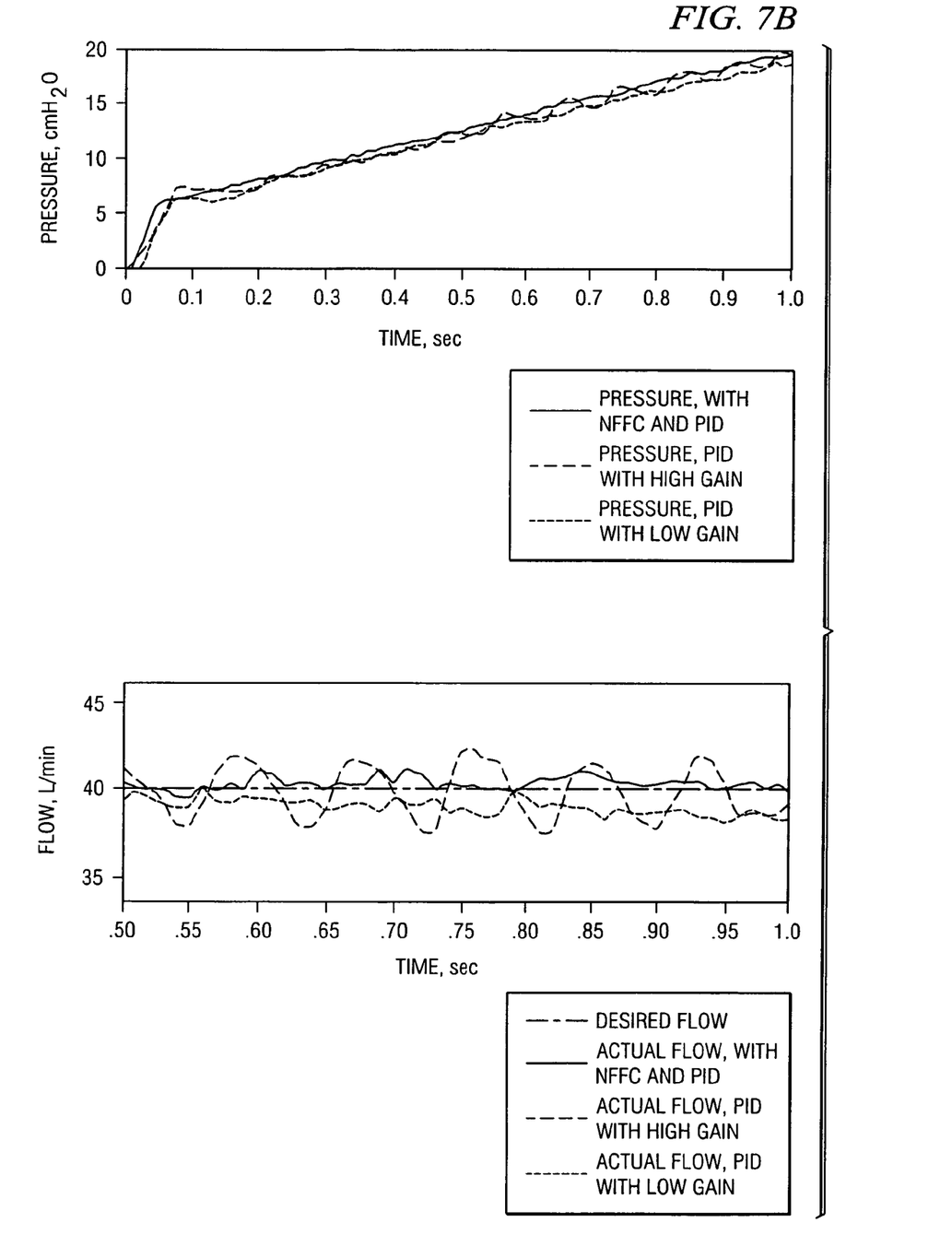

In FIGS. 7A and 7B, with a constant flow profile, the back pressure at the blower outlet kept increasing. A PID feedback controller with high gains was able to follow the profile, however with significant oscillations around the steady state value. Lowering the PID gains resulted in reduced oscillations at the price of increased steady state error. By applying a non-linear feedforward controller along with a PID feedback controller, the method achieved a better performance with reduced oscillations and smaller steady state error, as shown in FIG. 7B.

Figure 8A:
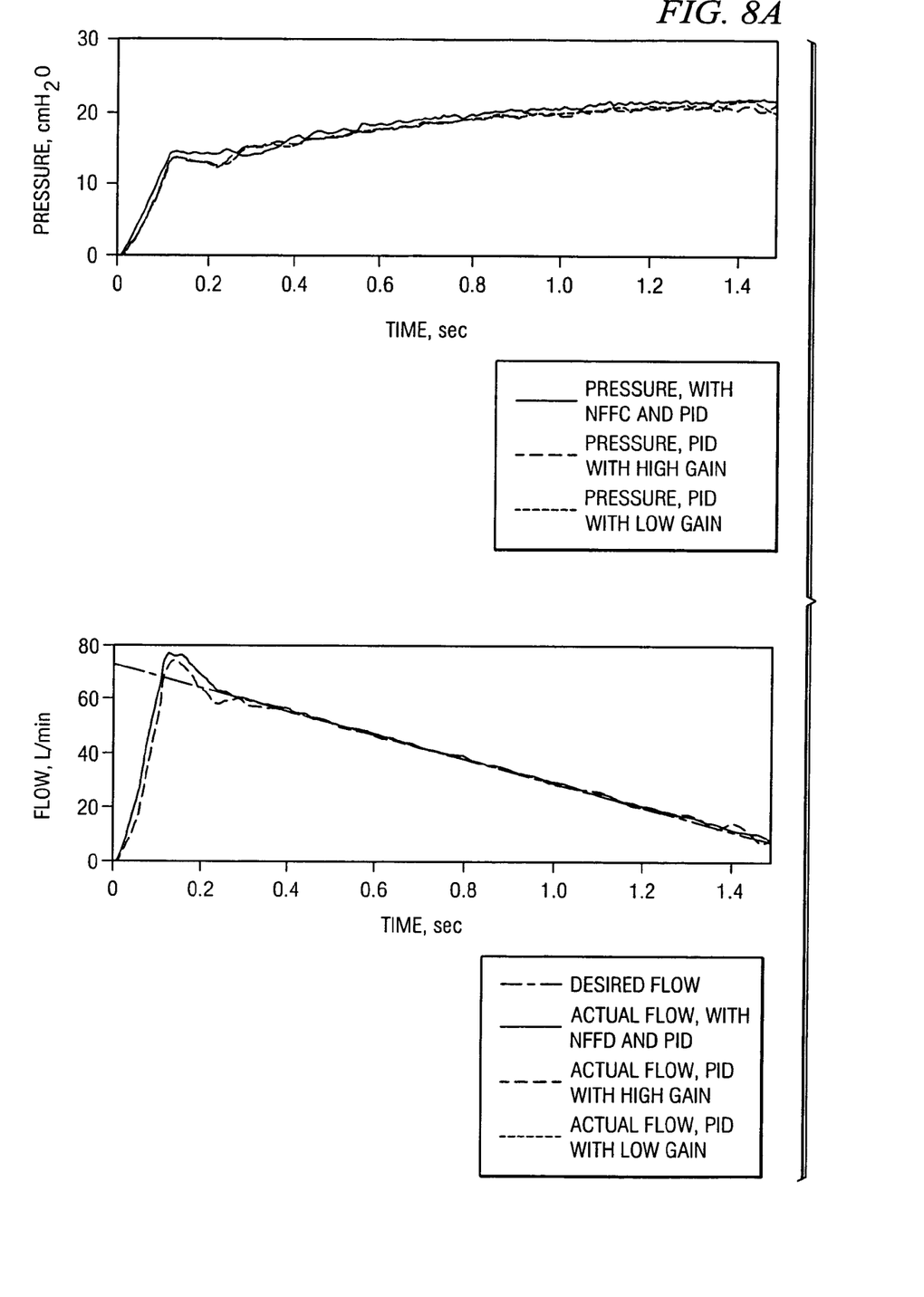
FIGS. 8A and 8B are graphs depicting the performance of control systems in an example requiring decreasing gas flow rate.
Figure 8B:
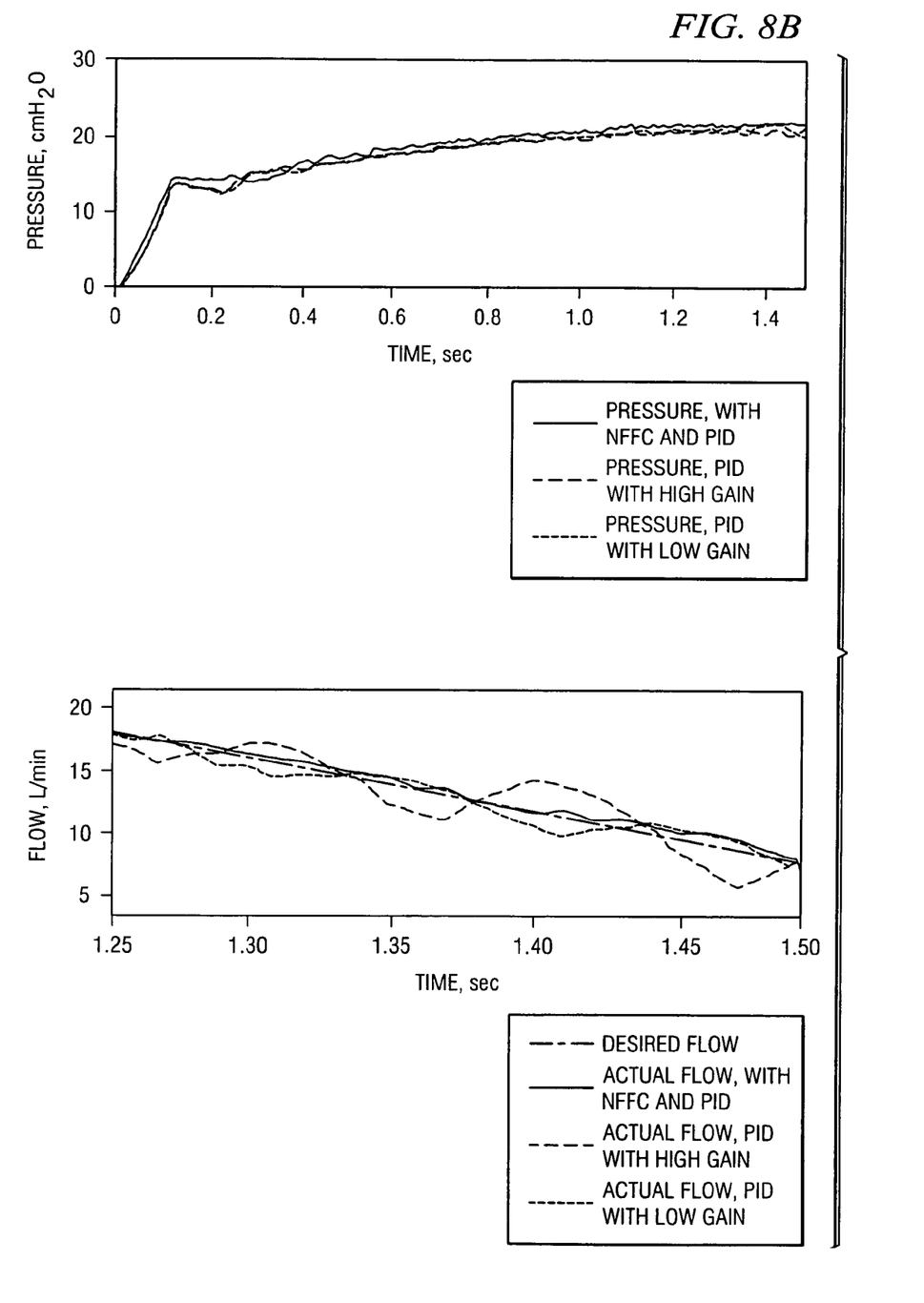

In FIGS. 8A and 8B, with a decreasing flow profile as the target flow rate, the back pressure at the blower outlet increased significantly at the beginning, and changed little afterwards. A PID feedback controller with high gains was able to follow the profile, however with oscillations around the profile towards the end of the profile. Lowering the PID gains resulted reduced oscillations. By applying non-linear feedforward controller and a PID feedback controller, the method achieved a better performance. Here the performance of PID with low gains is comparable to that of the non-linear feedforward controller. The reason is that after the initial stage, the disturbance (back pressure) does not change significantly. Therefore a PID controller was able to adapt to compensate for the disturbance. Still, non-linear feedforward controller was able to achieve a better performance as shown in FIG. 8B.

From the above, it may be seen that the present invention represents a novel and useful method and control system for controlling a medical ventilator. While several forms of the invention have been illustrated and described, it will be apparent that various modifications can be made without departing from the spirit and scope of the invention. Accordingly, it is not intended that the invention be limited other than by the scope of the appended claims.

I claim:

1. A method of controlling the rate of gas flow induced by a variable speed fan in a breathing assistance system, comprising the steps of:
   receiving a user setting for a target flow rate;
   measuring a back pressure experienced by the fan;
   calculating a target fan speed for producing the target flow rate set by the user based at least on the measured back pressure; and
   controlling the variable speed fan based at least on the calculated target fan speed.

2. The method of claim 1, further comprising the steps of:
   setting a time span for achieving the target flow rate; and
   repeating the entire process when the time span has concluded.

3. The method of claim 1, further comprising the steps of:
   measuring an actual flow rate generated by the fan;
   calculating the difference between the actual flow rate and the target flow rate; and
   controlling the variable speed fan based at least on (a) the measured back pressure and (b) the calculated difference between the actual flow rate and the target flow rate.

4. The method of claim 1, wherein:
   the fan includes a variable speed electric motor and a fan mechanism; and
   the setting the variable speed fan step includes sending a pulse width modulated electrical signal to the electric motor.

5. The method of claim 1, further comprising the steps of:
   measuring an actual fan speed;
   calculating a difference between the actual fan speed and the target fan speed calculated based on the measured back pressure; and
   controlling the variable speed fan based at least on the difference between the actual fan speed and the target fan speed calculated based on the measured back pressure.

6. The method of claim 1, comprising calculating the fan speed for producing the target flow rate using a non-linear function between fan speed, target flow rate, and current back pressure, wherein the non-linear function is preprogrammed into the breathing assistance system.

7. The method of claim 1, wherein the back pressure measured is that produced by a patient's lungs while the breathing assistance system is connected to the patient.

8. The method of claim 1, wherein each step is continued until the target flow rate is achieved.

9. A method of controlling a gas flow rate from a breathing assistance system, including the steps of:
   providing a breathing assistance system having a variable speed fan, an air hose, an electronic control system, an air flow transducer, and a pressure transducer;
   connecting the air hose of the breathing assistance system to a patient's lungs;
   repeatedly blowing air from the variable speed fan through the air hose and into the patient's lungs;
   monitoring the air flow through the air hose using the air flow transducer;
   monitoring the pressure within the air hose using the pressure transducer;
   using a feedforward controller of the electronic control system to calculate a first desired fan speed based at least on signals from the pressure transducer, including resolving a non-linear equation relating fan speed with gas flow rates and pressure;
   calculating a target fan speed using the electronic control system based at least on (a) signals from the air flow transducer and (b) the first desired fan speed calculated based at least on signals from the pressure transducer; and
   adjusting the variable speed fan based at least on the target fan speed.

10. The method of claim 9, further comprising the steps of:
    providing a speed transducer configured to measure the speed of the fan;
    monitoring an actual fan speed of the variable speed fan; and
    adjusting the variable speed fan to correct for differences between the actual fan speed and the target fan speed.

11. The method of claim 9, wherein the non-linear equation includes variables preprogrammed into the feedforward controller.

12. The method of claim 9, wherein the electronic control system further includes a feedback controller which calculates a second desired fan speed based at least on the air flow in the air hose, the second desired fan speed being used as input for calculating the target fan speed.

13. The method of claim 12, wherein the feedback controller and the feedforward controller work in unison to calculate the target fan speed based at least on both the air flow and pressure within the air hose.

14. The method of claim 12, wherein the feedback controller includes a proportional gain circuit, an integral gain circuit, and a differential gain circuit which together calculate the second desired fan speed.

15. The method of claim 14, wherein the proportional gain circuit, the integral gain circuit, and the differential gain circuit rely upon preprogrammed gain variables in their calculations.

16. A method of controlling the rate of gas flow induced by a fan including a fan outlet in a breathing assistance system, including the steps of:
    setting a target gas flow rate;
    setting a time span for the gas flow rate;
    calculating a first fan speed to induce the target flow rate within the time span;
    adjusting the fan based at least on the first fan speed;
    measuring a first gas flow rate generated by the fan at the conclusion of the time span;
    measuring a first back pressure experienced at the fan outlet at the conclusion of the time span;

calculating a second fan speed based at least on the first gas flow rate and the first back pressure to correct for the difference between the first gas flow rate and the target gas flow rate; and adjusting the fan based at least on the second fan speed.

17. The method of claim 16, wherein the setting a time span step includes setting a new time span each time a time span concludes, whereby the measuring, calculating and adjusting steps are repeated until inspiration is complete.

18. The method of claim 16, wherein calculating the second fan speed includes resolving a non-linear equation relating fan speed, back pressure, and the target gas flow rate.

19. The method of claim 18, wherein calculating the second fan speed further includes resolving a proportional-integral-derivative equation to correct for differences between the first gas flow rate and an actual gas flow rate to determine the second fan speed.

20. A system for controlling the gas flow induced by a breathing assistance system, comprising:
a variable speed motor connected to a fan having a fan outlet;
a first transducer configured to measure a pressure experienced at the fan outlet and to generate an electrical signal indicative of the pressure;
a second transducer configured to measure a rate of gas flow generated by the fan and to generate an electrical signal indicative of the gas flow rate;
an electronic feedforward control circuit configured to receive the electrical signal from the first transducer and to generate a first signal indicative of an adjustment to the speed of the variable speed motor;
an electronic feedback control circuit configured to receive the electrical signal from the second transducer and to generate a second signal indicative of an adjustment to the speed of the variable speed motor;
an electronic motor controller configured to vary the speed of the variable speed motor based at least on the first and second signals generated by the feedforward controller and the feedback controller;
a third transducer configured to measure the speed of the fan and to generate an electrical signal indicative of the fan speed; and
the electronic motor controller is further configured to receive the electrical signal generated by the third transducer.

21. The system of claim 20, further comprising:
a user interface configured to receive manual input of a target gas flow rate and to generate a signal indicative of the target gas flow rate; and
the electronic motor controller is further configured to receive the signal generated by the user interface.

22. The method of claim 1, wherein:
calculating the target fan speed for producing the target flow rate comprises calculating a target motor speed for a motor associated with the variable speed fan; and
controlling the variable speed fan based at least on the calculated target fan speed comprises controlling the motor based at least on the calculated target motor speed.

23. The method of claim 9, wherein:
calculating the target fan speed using the electronic control system comprises calculating a target motor speed for a motor associated with the variable speed fan; and adjusting the variable speed fan based at least on the target fan speed comprises adjusting the motor based at least on the calculated target motor speed.

24. The method of claim 16, wherein:
calculating the first fan speed comprises calculating a first motor speed for a motor associated with the fan;
adjusting the fan based at least on the first fan speed comprises adjusting the motor based at least on the calculated first motor speed;
calculating the first fan speed comprises calculating a second motor speed for the motor; and
adjusting the fan based at least on the second fan speed comprises adjusting the motor based at least on the calculated second motor speed.

25. A method of controlling a breathing assistance system including a variable speed fan, an air conduit, an air flow sensor, a pressure sensor, and a fan speed sensor, the method comprising:
monitoring air flow through the air conduit using the air flow sensor;
monitoring pressure within the air conduit using the pressure sensor;
calculating a target fan speed based at least on signals from the air flow sensor and the pressure sensor;
adjusting the variable speed fan based at least on the target fan speed;
monitoring an actual fan speed of the variable speed fan; and
adjusting the variable speed fan to correct for differences between the actual fan speed and the target fan speed.

26. A method of controlling the rate of gas flow induced by a variable speed fan in a breathing assistance system, comprising the steps of:
setting a target flow rate;
measuring an actual flow rate generated by the fan;
calculating the difference between the actual flow rate and the target flow rate;
measuring a back pressure experienced by the fan;
calculating a target fan speed for producing the target flow rate set based at least on the measured back pressure and the difference between the actual flow rate and the target flow rate; and
controlling the variable speed fan based at least on the target fan speed.

27. A method of controlling the rate of gas flow induced by a variable speed fan in a breathing assistance system, comprising the steps of:
setting a target flow rate;
measuring a back pressure experienced by the fan;
calculating a target fan speed for producing the target flow rate set based at least on the measured back pressure;
controlling the variable speed fan based at least on the calculated target fan speed;
measuring an actual fan speed;
calculating a difference between the actual fan speed and the target fan speed calculated based on the measured back pressure; and
controlling the variable speed fan based at least on the difference between the actual fan speed and the target fan speed calculated based on the measured back pressure.

* * * * *